(12) United States Patent
Dahla et al.

(10) Patent No.: US 8,323,279 B2
(45) Date of Patent: *Dec. 4, 2012

(54) SYSTEM, METHOD AND APPARATUS FOR ELECTROSURGICAL INSTRUMENT WITH MOVABLE FLUID DELIVERY SHEATH

(75) Inventors: Robert H. Dahla, Sunnyvale, CA (US); Irma Gutierrez, San Jose, CA (US)

(73) Assignee: ArthoCare Corporation, Austin, TX (US)

( * ) Notice: Subject to any disclaimer, the term of this patent is extended or adjusted under 35 U.S.C. 154(b) by 594 days.

This patent is subject to a terminal disclaimer.

(21) Appl. No.: 12/566,946

(22) Filed: Sep. 25, 2009

(65) Prior Publication Data

US 2011/0077646 A1 Mar. 31, 2011

(51) Int. Cl.
*A61B 18/18* (2006.01)
*A61M 1/00* (2006.01)
(52) U.S. Cl. .......... 606/48; 606/41; 604/30; 604/33
(58) Field of Classification Search .......... 606/48, 606/50; 604/33, 27, 35, 158, 163, 164.02, 604/181, 183, 118–121, 30, 40, 508; 251/267
See application file for complete search history.

(56) References Cited

U.S. PATENT DOCUMENTS

| | | | |
|---|---|---|---|
| 2,050,904 A | 8/1936 | Trice | 219/233 |
| 2,056,377 A | 10/1939 | Wappler | 125/303 |
| 2,275,167 A | 3/1942 | Bierman | 606/50 |
| 3,633,425 A | 1/1972 | Sanford | 73/356 |
| 3,699,967 A | 10/1972 | Anderson | 606/37 |
| 3,812,858 A | 5/1974 | Oringer | 604/22 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |

(Continued)

FOREIGN PATENT DOCUMENTS

DE 2521719 11/1976

(Continued)

OTHER PUBLICATIONS

EP Search Report for EP 07118068 3pgs, Mailed Dec. 27, 2010.

(Continued)

*Primary Examiner* — Linda Dvorak
*Assistant Examiner* — Jaymi Della
(74) *Attorney, Agent, or Firm* — Matthew Scheele; Brian Szymczak

(57) ABSTRACT

An electrosurgical instrument with a movable fluid delivery sheath assembly for variable fluid supply during surgical procedures is disclosed. The instrument comprises at least one active electrode and at least one return electrode, positioned on the instrument distal end. The sheath assembly has an outer sheath that is external to the instrument shaft, to provide a lumen. The sheath assembly lumen is axially movable between first and second positions relative to a fluid delivery element, for varying target site treatment and fluid delivery. In the first position the shaft distal end is axially distal to a leading edge of the sheath assembly. In the second position the sheath assembly distal leading edge is positioned axially adjacent or distal to the end of the shaft. The fluid delivery element comprises an inner lumen extending through at least a portion of the shaft, and at least one port extending radially through the shaft. The port is in communication with the inner lumen. A fluid supply source provides fluid through the port, sheath lumen and inner lumen.

15 Claims, 7 Drawing Sheets

U.S. PATENT DOCUMENTS

| | | | | |
|---|---|---|---|---|
| 3,945,375 A | 3/1976 | Banko | | 600/104 |
| 3,970,088 A | 7/1976 | Morrison | | 128/303 |
| 4,033,351 A | 7/1977 | Hetzel | | 606/48 |
| 4,040,426 A | 8/1977 | Morrison, Jr. | | 128/303 |
| 4,043,342 A | 8/1977 | Morrison, Jr. | | 128/303 |
| 4,074,718 A | 2/1978 | Morrison, Jr. | | 128/303 |
| 4,092,986 A | 6/1978 | Schneiderman | | 128/303 |
| 4,116,198 A | 9/1978 | Roos | | 128/303 |
| 4,181,131 A | 1/1980 | Ogiu | | 128/303 |
| 4,184,492 A | 1/1980 | Meinke et al. | | 128/303 |
| 4,202,337 A | 5/1980 | Hren et al. | | 128/303 |
| 4,203,444 A | 5/1980 | Bonnell et al. | | 604/22 |
| 4,228,800 A | 10/1980 | Degler, Jr. et al. | | 128/303 |
| 4,232,676 A | 11/1980 | Herczog | | 128/303 |
| 4,240,441 A | 12/1980 | Khalil | | 128/692 |
| 4,248,231 A | 2/1981 | Herczog et al. | | 128/303 |
| 4,269,174 A | 5/1981 | Adair | | 128/842 |
| 4,326,529 A | 4/1982 | Doss et al. | | 128/303 |
| 4,381,007 A | 4/1983 | Doss | | 128/303 |
| 4,411,266 A | 10/1983 | Cosman | | 606/49 |
| 4,429,694 A | 2/1984 | McGreevy | | 128/303.14 |
| 4,474,179 A | 10/1984 | Koch | | 606/40 |
| 4,476,862 A | 10/1984 | Pao | | 128/303 |
| 4,483,338 A | 11/1984 | Bloom et al. | | 606/50 |
| 4,532,924 A | 8/1985 | Auth et al. | | 128/303 |
| 4,548,207 A | 10/1985 | Reimels | | 128/303 |
| 4,567,890 A | 2/1986 | Ohta et al. | | 128/303 |
| 4,582,057 A | 4/1986 | Auth et al. | | 606/31 |
| 4,590,934 A | 5/1986 | Malis et al. | | 128/303 |
| 4,593,691 A | 6/1986 | Lindstrom et al. | | 128/303 |
| 4,641,649 A | 2/1987 | Walinsky | | 606/33 |
| 4,658,817 A | 4/1987 | Hardy | | 606/14 |
| 4,660,571 A | 4/1987 | Hess et al. | | 128/784 |
| 4,674,499 A | 6/1987 | Pao | | 128/303 |
| 4,675,499 A | 6/1987 | Nakai | | 128/303 |
| 4,682,596 A | 7/1987 | Bales et al. | | 128/303 |
| 4,706,667 A | 11/1987 | Roos | | 128/303 |
| 4,709,698 A | 12/1987 | Johnston et al. | | 128/303 |
| 4,719,914 A * | 1/1988 | Johnson | | 606/28 |
| 4,727,874 A | 3/1988 | Bowers et al. | | 128/303 |
| 4,736,743 A | 4/1988 | Daikuzono | | 128/303.1 |
| 4,737,678 A | 4/1988 | Hasegawa | | 313/36 |
| 4,762,128 A | 8/1988 | Rosenbluth | | 128/343 |
| 4,765,331 A | 8/1988 | Petruzzi et al. | | 128/303 |
| 4,785,806 A | 11/1988 | Deckelbaum | | 128/303.1 |
| 4,785,823 A | 11/1988 | Eggers et al. | | 128/692 |
| 4,805,616 A | 2/1989 | Pao | | 128/303 |
| 4,813,429 A | 3/1989 | Eshel et al. | | 128/736 |
| 4,823,791 A | 4/1989 | D'Amelio et al. | | 123/303 |
| 4,827,911 A | 5/1989 | Broadwin et al. | | 604/22 |
| 4,832,048 A | 5/1989 | Cohen | | 128/786 |
| 4,860,752 A | 8/1989 | Turner et al. | | 128/422 |
| 4,903,696 A | 2/1990 | Stasz et al. | | 606/37 |
| 4,907,589 A | 3/1990 | Cosman | | 606/34 |
| 4,920,978 A | 5/1990 | Colvin | | 128/784 |
| 4,931,047 A | 6/1990 | Broadwin et al. | | 604/22 |
| 4,936,281 A | 6/1990 | Stasz | | 128/660 |
| 4,936,301 A | 6/1990 | Rexroth et al. | | 606/45 |
| 4,940,064 A | 7/1990 | Desai | | 607/122 |
| 4,943,290 A | 7/1990 | Rexroth et al. | | 606/45 |
| 4,955,377 A | 9/1990 | Lennox et al. | | 128/401 |
| 4,966,597 A | 10/1990 | Cosman | | 606/50 |
| 4,967,765 A | 11/1990 | Turner et al. | | 128/784 |
| 4,968,314 A | 11/1990 | Michaels | | 606/7 |
| 4,976,709 A | 12/1990 | Sand | | 606/5 |
| 4,976,711 A | 12/1990 | Parins et al. | | 606/48 |
| 4,979,948 A | 12/1990 | Geddes et al. | | 606/33 |
| 4,998,933 A | 3/1991 | Eggers et al. | | 606/41 |
| 5,007,437 A | 4/1991 | Sterzer | | 428/786 |
| 5,007,908 A | 4/1991 | Rydell | | 606/47 |
| 5,009,656 A | 4/1991 | Reimels | | 606/48 |
| 5,035,696 A | 7/1991 | Rydell | | 606/47 |
| 5,037,421 A | 8/1991 | Boutacoff et al. | | 606/15 |
| 5,047,026 A | 9/1991 | Rydell | | 606/48 |
| 5,047,027 A | 9/1991 | Rydell | | 606/48 |
| 5,057,105 A | 10/1991 | Malone et al. | | 606/28 |
| 5,057,106 A | 10/1991 | Kasevich et al. | | 606/33 |
| 5,061,266 A | 10/1991 | Hakky | | 606/15 |
| 5,078,717 A | 1/1992 | Parins et al. | | 606/48 |
| 5,080,660 A | 1/1992 | Buelna | | 606/45 |
| 5,083,565 A | 1/1992 | Parins | | 128/642 |
| 5,084,044 A | 1/1992 | Quint | | 606/27 |
| 5,084,045 A * | 1/1992 | Helenowski | | 606/32 |
| 5,085,659 A | 2/1992 | Rydell | | 606/47 |
| 5,088,997 A | 2/1992 | Delahuerga et al. | | 606/42 |
| 5,092,339 A | 3/1992 | Geddes et al. | | 128/692 |
| 5,093,877 A | 3/1992 | Aita et al. | | 385/34 |
| 5,098,431 A | 3/1992 | Rydell | | 606/48 |
| 5,099,840 A | 3/1992 | Goble | | 128/422 |
| 5,102,410 A | 4/1992 | Dressel | | 606/15 |
| 5,103,804 A | 4/1992 | Abele et al. | | 600/116 |
| 5,108,391 A | 4/1992 | Flachenecker et al. | | 606/38 |
| RE33,925 E | 5/1992 | Bales et al. | | 606/48 |
| 5,112,330 A | 5/1992 | Nishigaki et al. | | 606/46 |
| 5,122,138 A | 6/1992 | Manwaring | | 606/46 |
| 5,125,928 A | 6/1992 | Parins et al. | | 606/48 |
| 5,137,530 A | 8/1992 | Sand | | 606/5 |
| 5,147,354 A | 9/1992 | Boutacoff et al. | | 606/15 |
| 5,151,098 A | 9/1992 | Loertscher | | 606/16 |
| 5,156,151 A | 10/1992 | Imran | | 600/375 |
| 5,167,659 A | 12/1992 | Ohtomo et al. | | 606/40 |
| 5,171,311 A | 12/1992 | Rydell et al. | | 606/48 |
| 5,176,528 A | 1/1993 | Fry et al. | | 439/181 |
| 5,178,620 A | 1/1993 | Eggers et al. | | 606/41 |
| 5,190,517 A | 3/1993 | Zieve et al. | | 604/22 |
| 5,191,883 A | 3/1993 | Lennox et al. | | 607/102 |
| 5,192,280 A | 3/1993 | Parins | | 606/48 |
| 5,195,959 A | 3/1993 | Smith | | 604/34 |
| 5,197,466 A | 3/1993 | Marchosky et al. | | 128/399 |
| 5,197,963 A | 3/1993 | Parins | | 606/46 |
| 5,207,675 A | 5/1993 | Canady | | 606/40 |
| 5,217,455 A | 6/1993 | Tan | | 606/9 |
| 5,217,457 A | 6/1993 | Delahuerga et al. | | 606/42 |
| 5,217,459 A | 6/1993 | Kamerling | | 606/48 |
| 5,230,334 A | 7/1993 | Klopotek | | 601/3 |
| 5,234,428 A | 8/1993 | Kaufman | | 606/45 |
| 5,246,438 A | 9/1993 | Langberg | | 606/33 |
| 5,249,585 A | 10/1993 | Turner et al. | | 607/99 |
| 5,261,410 A | 11/1993 | Alfano et al. | | 600/475 |
| 5,267,994 A | 12/1993 | Gentelia et al. | | 606/15 |
| 5,267,997 A | 12/1993 | Farin et al. | | 606/38 |
| 5,269,794 A | 12/1993 | Rexroth | | 606/180 |
| 5,273,524 A | 12/1993 | Fox et al. | | 604/21 |
| 5,277,201 A | 1/1994 | Stern | | 607/98 |
| 5,277,696 A | 1/1994 | Hagen | | 606/49 |
| 5,279,299 A | 1/1994 | Imran | | 600/393 |
| 5,281,216 A | 1/1994 | Klicek | | 606/42 |
| 5,281,218 A | 1/1994 | Imran | | 606/41 |
| 5,282,797 A | 2/1994 | Chess | | 606/9 |
| 5,282,799 A | 2/1994 | Rydell | | 606/48 |
| 5,290,273 A | 3/1994 | Tan | | 606/9 |
| 5,290,282 A | 3/1994 | Casscells | | 606/29 |
| 5,293,868 A | 3/1994 | Nardella | | 600/373 |
| 5,295,956 A * | 3/1994 | Bales et al. | | 604/30 |
| 5,300,069 A | 4/1994 | Hunsberger et al. | | 606/37 |
| 5,300,099 A | 4/1994 | Rudie | | 607/101 |
| 5,301,687 A | 4/1994 | Wong et al. | | 607/116 |
| 5,304,169 A | 4/1994 | Sand | | 606/5 |
| 5,304,170 A | 4/1994 | Green | | 606/9 |
| 5,306,238 A | 4/1994 | Fleenor | | 606/42 |
| 5,312,395 A | 5/1994 | Tan et al. | | 606/9 |
| 5,312,400 A | 5/1994 | Bales et al. | | 606/41 |
| 5,314,406 A | 5/1994 | Arias et al. | | 604/21 |
| 5,318,563 A | 6/1994 | Malis et al. | | 606/38 |
| 5,322,507 A | 6/1994 | Costello et al. | | 128/4 |
| 5,324,254 A | 6/1994 | Phillips | | 604/21 |
| 5,330,470 A | 7/1994 | Hagen | | 606/42 |
| 5,330,518 A | 7/1994 | Neilson et al. | | 607/101 |
| 5,334,140 A | 8/1994 | Philips | | 604/35 |
| 5,334,183 A | 8/1994 | Wuchinich | | 606/46 |
| 5,334,193 A | 8/1994 | Nardella | | 606/41 |
| 5,335,668 A | 8/1994 | Nardella | | 600/547 |
| 5,336,217 A | 8/1994 | Buys et al. | | 606/9 |
| 5,336,220 A | 8/1994 | Ryan et al. | | 604/22 |
| 5,336,443 A | 8/1994 | Eggers | | 252/511 |
| 5,342,357 A | 8/1994 | Nardella | | 606/40 |
| 5,348,554 A | 9/1994 | Imran et al. | | 606/41 |

| Patent | Date | Inventor | Class |
|---|---|---|---|
| 5,366,443 A | 11/1994 | Odashima | 604/114 |
| 5,370,642 A | 12/1994 | Keller | 606/9 |
| 5,370,644 A | 12/1994 | Langberg | 606/33 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,395,363 A | 3/1995 | Billings et al. | 606/41 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,405,376 A | 4/1995 | Mulier et al. | 607/127 |
| 5,417,687 A | 5/1995 | Nardella et al. | 606/32 |
| 5,419,767 A | 5/1995 | Eggers et al. | 604/114 |
| 5,423,803 A | 6/1995 | Tankovich | 606/9 |
| 5,423,810 A | 6/1995 | Goble et al. | 606/40 |
| 5,423,844 A | 6/1995 | Miller | 606/171 |
| 5,423,882 A | 6/1995 | Jackman et al. | 607/122 |
| 5,431,649 A | 7/1995 | Mulier et al. | 606/41 |
| 5,432,882 A | 7/1995 | Glynn | 607/122 |
| 5,433,708 A | 7/1995 | Nichols et al. | 604/113 |
| 5,436,566 A | 7/1995 | Thompson et al. | 324/713 |
| 5,437,662 A | 8/1995 | Nardella | 606/40 |
| 5,437,664 A | 8/1995 | Cohen et al. | 606/42 |
| 5,438,302 A | 8/1995 | Goble | 331/167 |
| 5,441,499 A | 8/1995 | Fritzsch | 606/45 |
| 5,445,634 A | 8/1995 | Keller | 606/9 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,462,545 A | 10/1995 | Wang et al. | 606/41 |
| 5,484,435 A | 1/1996 | Fleenor et al. | 606/46 |
| 5,487,385 A | 1/1996 | Avitall | 600/374 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,710 A * | 4/1996 | Dorsey, III | 604/158 |
| 5,514,130 A | 5/1996 | Baker | 606/41 |
| 5,520,685 A | 5/1996 | Wojciechowicz | 606/49 |
| 5,536,267 A * | 7/1996 | Edwards et al. | 606/41 |
| 5,542,928 A | 8/1996 | Evans et al. | 604/113 |
| 5,545,161 A | 8/1996 | Imran | 606/41 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,579,764 A | 12/1996 | Goldreyer | 600/374 |
| 5,584,872 A | 12/1996 | LaFontaine et al. | 607/117 |
| 5,607,391 A * | 3/1997 | Klinger et al. | 604/33 |
| 5,607,421 A | 3/1997 | Jeevanandam et al. | 606/15 |
| 5,609,151 A | 3/1997 | Mulier et al. | 128/642 |
| 5,626,576 A * | 5/1997 | Janssen | 606/41 |
| 5,633,578 A | 5/1997 | Eggers et al. | 323/301 |
| 5,643,255 A | 7/1997 | Organ | 606/41 |
| 5,647,869 A | 7/1997 | Goble et al. | 606/37 |
| 5,653,692 A | 8/1997 | Masterson et al. | 604/113 |
| 5,660,836 A | 8/1997 | Knowlton | 607/101 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,681,308 A | 10/1997 | Edwards et al. | 606/41 |
| 5,683,366 A | 11/1997 | Eggers et al. | 604/114 |
| 5,688,267 A | 11/1997 | Panescu et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,713,896 A | 2/1998 | Nardella | 606/50 |
| 5,725,524 A | 3/1998 | Mulier et al. | 606/41 |
| 5,743,870 A | 4/1998 | Edwards | 604/22 |
| 5,743,903 A | 4/1998 | Stern et al. | 606/31 |
| 5,746,746 A | 5/1998 | Garito et al. | 606/41 |
| 5,749,869 A | 5/1998 | Lindenmeier et al. | 606/34 |
| 5,755,753 A | 5/1998 | Knowlton | 607/98 |
| 5,766,153 A | 6/1998 | Eggers et al. | 604/114 |
| 5,769,843 A | 6/1998 | Abela et al. | 606/10 |
| 5,769,847 A | 6/1998 | Panescu et al. | 606/42 |
| 5,782,795 A | 7/1998 | Bays | 604/22 |
| 5,785,705 A | 7/1998 | Baker | 606/32 |
| 5,800,429 A | 9/1998 | Edwards | 606/41 |
| 5,800,431 A | 9/1998 | Brown | 606/42 |
| 5,807,384 A | 9/1998 | Mueller | 606/7 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,843,078 A | 12/1998 | Sharkey | 606/41 |
| 5,855,277 A | 1/1999 | Apps et al. | 606/35 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,871,524 A | 2/1999 | Knowlton | 607/101 |
| 5,873,855 A | 2/1999 | Eggers et al. | 604/114 |
| 5,876,398 A | 3/1999 | Mulier et al. | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,893,848 A | 4/1999 | Negus et al. | 606/41 |
| 5,895,386 A | 4/1999 | Odell et al. | 606/50 |
| 5,897,553 A | 4/1999 | Mulier | 606/41 |
| 5,902,272 A | 5/1999 | Eggers et al. | 604/114 |
| 5,904,681 A | 5/1999 | West, Jr. | 606/41 |
| 5,906,613 A | 5/1999 | Mulier et al. | 606/41 |
| 5,919,219 A | 7/1999 | Knowlton | 607/102 |
| 5,944,715 A | 8/1999 | Goble et al. | 606/41 |
| 5,954,716 A | 9/1999 | Sharkey et al. | 606/32 |
| 5,964,754 A | 10/1999 | Osypka | 606/37 |
| 5,976,127 A | 11/1999 | Lax | 606/32 |
| 5,980,516 A | 11/1999 | Mulier et al. | 606/41 |
| 5,980,545 A | 11/1999 | Pacala et al. | 606/170 |
| 5,984,919 A | 11/1999 | Hilal et al. | 606/45 |
| 6,004,319 A | 12/1999 | Goble et al. | 606/48 |
| 6,007,533 A | 12/1999 | Casscells et al. | 606/45 |
| 6,007,570 A | 12/1999 | Sharkey et al. | 607/96 |
| 6,013,076 A | 1/2000 | Goble et al. | 606/41 |
| 6,015,406 A | 1/2000 | Goble et al. | 606/41 |
| 6,016,809 A | 1/2000 | Mulier et al. | 128/898 |
| 6,024,733 A | 2/2000 | Eggers et al. | 604/500 |
| 6,027,501 A | 2/2000 | Goble et al. | 606/41 |
| 6,030,383 A | 2/2000 | Benderev | 606/45 |
| 6,032,673 A | 3/2000 | Savage et al. | 128/898 |
| 6,032,674 A | 3/2000 | Eggers et al. | 606/41 |
| 6,039,734 A | 3/2000 | Goble et al. | 606/41 |
| 6,042,580 A | 3/2000 | Simpson | 606/32 |
| 6,045,532 A | 4/2000 | Eggers et al. | 604/114 |
| 6,047,700 A | 4/2000 | Eggers et al. | 128/898 |
| 6,053,172 A | 4/2000 | Hovda et al. | 128/898 |
| 6,056,746 A | 5/2000 | Goble et al. | 606/48 |
| 6,063,079 A | 5/2000 | Hovda et al. | 606/41 |
| 6,063,081 A | 5/2000 | Mulier et al. | 606/45 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,091,995 A | 7/2000 | Ingle et al. | 607/138 |
| 6,093,186 A | 7/2000 | Goble et al. | 606/34 |
| 6,096,037 A | 8/2000 | Mulier et al. | 606/49 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,110,169 A | 8/2000 | Mueller et al. | 606/48 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |

| Patent No. | Date | Inventor | Class |
|---|---|---|---|
| 6,152,923 A | 11/2000 | Ryan | 606/51 |
| 6,156,031 A | 12/2000 | Aita et al. | 606/33 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,214,001 B1 | 4/2001 | Casscells et al. | 606/41 |
| 6,217,575 B1 | 4/2001 | DeVore et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Eggers | 606/32 |
| 6,235,020 B1 | 5/2001 | Cheng et al. | 606/34 |
| 6,235,023 B1 | 5/2001 | Lee et al. | 606/41 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 607/127 |
| 6,254,600 B1 | 7/2001 | Willink et al. | 606/41 |
| 6,261,286 B1 | 7/2001 | Goble et al. | 606/34 |
| 6,261,311 B1 | 7/2001 | Sharkey et al. | 607/96 |
| 6,264,650 B1 | 7/2001 | Hovda | 606/32 |
| 6,264,652 B1 | 7/2001 | Eggers et al. | 606/41 |
| 6,267,757 B1 | 7/2001 | Aita et al. | 606/33 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 606/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,302,903 B1 | 10/2001 | Mulier et al. | 607/105 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,312,429 B1 | 11/2001 | Butbank et al. | 606/47 |
| 6,315,774 B1 | 11/2001 | Daniel et al. | 606/15 |
| 6,322,494 B1 | 11/2001 | Bullivant et al. | 600/104 |
| 6,322,549 B1 | 11/2001 | Eggers et al. | 604/500 |
| 6,325,799 B1 | 12/2001 | Goble | 606/41 |
| 6,327,505 B1 | 12/2001 | Medhkour et al. | 607/99 |
| 6,328,736 B1 | 12/2001 | Mulier et al. | 606/45 |
| 6,336,926 B1 | 1/2002 | Goble | 606/34 |
| 6,346,107 B1 | 2/2002 | Cucin | 606/49 |
| 6,355,006 B1 | 3/2002 | Ryaby et al. | 601/2 |
| 6,355,032 B1 | 3/2002 | Hovda et al. | 606/32 |
| 6,358,248 B1 | 3/2002 | Mulier et al. | 606/41 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,391,025 B1 | 5/2002 | Weinstein et al. | 606/41 |
| 6,391,028 B1 | 5/2002 | Fanton et al. | 606/45 |
| 6,398,781 B1 | 6/2002 | Gobel et al. | 606/41 |
| 6,409,724 B1 | 6/2002 | Penny et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,432,105 B1 | 8/2002 | Ellman et al. | 606/48 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,482,202 B1 | 11/2002 | Goble et al. | 606/41 |
| 6,491,690 B1 | 12/2002 | Gobel et al. | 606/41 |
| 6,497,705 B2* | 12/2002 | Comben | 606/41 |
| 6,497,706 B1* | 12/2002 | Burbank et al. | 606/45 |
| 6,510,854 B2 | 1/2003 | Gobel | 128/898 |
| 6,514,250 B1 | 2/2003 | Jahns et al. | 606/41 |
| 6,517,498 B1 | 2/2003 | Burbank et al. | 600/564 |
| 6,517,535 B2 | 2/2003 | Edwards | 606/41 |
| 6,530,922 B2 | 3/2003 | Cosman | 606/34 |
| 6,540,741 B1 | 4/2003 | Underwood et al. | 606/32 |
| 6,557,559 B1 | 5/2003 | Eggers et al. | 128/898 |
| 6,575,968 B1 | 6/2003 | Eggers et al. | 606/41 |
| 6,575,969 B1 | 6/2003 | Rittman, III et al. | 606/41 |
| 6,578,579 B2 | 6/2003 | Burnside | 128/897 |
| 6,582,423 B1 | 6/2003 | Thapliyal et al. | 606/32 |
| 6,589,237 B2 | 7/2003 | Woloszko et al. | 606/41 |
| 6,595,990 B1 | 7/2003 | Weinstein et al. | 606/41 |
| 6,597,950 B2 | 7/2003 | Linder et al. | 607/8 |
| 6,602,248 B1 | 8/2003 | Sharps et al. | 606/32 |
| 6,605,085 B1 | 8/2003 | Edwards | 606/41 |
| 6,610,059 B1 | 8/2003 | West, Jr. | 606/41 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,632,230 B2 | 10/2003 | Barry | 606/159 |
| 6,645,203 B2 | 11/2003 | Sharkey et al. | 606/41 |
| 6,663,628 B2 | 12/2003 | Peters | 606/45 |
| 6,695,839 B2 | 2/2004 | Sharkey et al. | 606/49 |
| 6,699,206 B2 | 3/2004 | Burbank et al. | 606/567 |
| 6,699,244 B2 | 3/2004 | Carranza et al. | 606/41 |
| 6,702,810 B2 | 3/2004 | McClurken et al. | 606/34 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| 6,763,836 B2 | 7/2004 | Tasto et al. | 128/898 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,796,982 B2 | 9/2004 | Carmel et al. | 606/41 |
| 6,802,842 B2 | 10/2004 | Ellman et al. | 606/45 |
| 6,805,130 B2 | 10/2004 | Tasto et al. | 606/32 |
| 6,827,725 B2 | 12/2004 | Batchelor et al. | 606/170 |
| 6,832,996 B2 | 12/2004 | Woloszko et al. | 606/41 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,896,674 B1 | 5/2005 | Woloszko et al. | 606/41 |
| 6,904,303 B2 | 6/2005 | Phan et al. | 600/374 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,332 B2 | 12/2005 | Adams | 606/45 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,150,747 B1 | 12/2006 | McDonald et al. | 606/45 |
| 7,169,143 B2 | 1/2007 | Eggers et al. | 606/32 |
| 7,179,255 B2 | 2/2007 | Lettice et al. | 606/32 |
| 7,184,811 B2 | 2/2007 | Phan et al. | 600/374 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,258,690 B2 | 8/2007 | Sutton et al. | 606/45 |
| 7,261,712 B2 | 8/2007 | Burbank et al. | 606/49 |
| 7,270,658 B2 | 9/2007 | Woloszko et al. | 606/32 |
| 7,270,659 B2 | 9/2007 | Ricart et al. | 606/32 |
| 7,270,661 B2 | 9/2007 | Dahla et al. | 606/41 |
| 7,276,063 B2 | 10/2007 | Davison et al. | 606/45 |
| 7,297,143 B2 | 11/2007 | Woloszko et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |

| | | | | | | |
|---|---|---|---|---|---|---|
| 7,435,247 | B2 | 10/2008 | Woloszko et al. ............... 604/45 | EP | 0740926 A2 | 11/1996 |
| 7,442,191 | B2 | 10/2008 | Hovda et al. ................... 606/41 | EP | 0 754 437 | 1/1997 |
| 7,445,618 | B2 | 11/2008 | Eggers et al. ................... 604/48 | EP | 923907 | 6/1999 |
| 7,449,021 | B2 | 11/2008 | Underwood et al. ............ 606/32 | EP | 0 694 290 | 11/2000 |
| 7,462,178 | B2 | 12/2008 | Woloszko et al. ............. 607/105 | EP | 1149564 | 10/2001 |
| 7,468,059 | B2 | 12/2008 | Eggers et al. ................... 606/32 | EP | 1041933 | 3/2004 |
| 7,488,295 | B2 | 2/2009 | Burbank et al. ................ 606/167 | FR | 2313949 | 1/1977 |
| 7,491,200 | B2 | 2/2009 | Underwood et al. ............ 606/32 | GB | 2037167 | 7/1980 |
| 7,507,236 | B2 | 3/2009 | Eggers et al. ................... 606/41 | GB | 2 308 979 | 7/1997 |
| 7,572,251 | B1 | 8/2009 | Davison et al. ................ 604/500 | GB | 2 308 980 | 7/1997 |
| 7,819,863 | B2 | 10/2010 | Eggers et al. ................... 606/32 | GB | 2 308 981 | 7/1997 |
| 2002/0029036 | A1 | 3/2002 | Goble et al. ..................... 606/38 | GB | 2 327 350 | 1/1999 |
| 2002/0049438 | A1 | 4/2002 | Sharkey et al. ................. 606/41 | GB | 2 327 351 | 1/1999 |
| 2002/0072739 | A1 | 6/2002 | Lee et al. ........................ 606/47 | GB | 2 327 352 | 1/1999 |
| 2003/0013986 | A1 | 1/2003 | Saadat .......................... 600/549 | GB | 2331247 | 5/1999 |
| 2003/0088245 | A1 | 5/2003 | Woloszko et al. ............... 606/41 | GB | 2379878 | 3/2003 |
| 2003/0130655 | A1 | 7/2003 | Woloszko et al. ............... 606/45 | GB | 2408936 | 6/2005 |
| 2003/0130711 | A1 | 7/2003 | Pearson et al. ................. 607/101 | JP | 57-57802 | 4/1982 |
| 2003/0158545 | A1 | 8/2003 | Hovda et al. ................... 606/32 | JP | 57-117843 | 7/1982 |
| 2003/0171743 | A1 | 9/2003 | Tasto et al. ..................... 606/32 | JP | 57-183850 | 11/1982 |
| 2003/0208196 | A1 | 11/2003 | Stone .............................. 606/41 | JP | 63-40099 | 8/1988 |
| 2003/0212396 | A1 | 11/2003 | Eggers et al. ................... 606/41 | JP | 9-501328 | 2/1997 |
| 2004/0116922 | A1 | 6/2004 | Hovda et al. ................... 606/41 | WO | 90/03152 | 4/1990 |
| 2004/0127893 | A1 | 7/2004 | Hovda ............................ 606/41 | WO | 90/07303 | 7/1990 |
| 2004/0230190 | A1 | 11/2004 | Dahla et al. .................... 604/41 | WO | 91/13650 | 9/1991 |
| 2005/0004634 | A1 | 1/2005 | Ricart et al. .................... 606/41 | WO | 92/21278 | 12/1992 |
| 2005/0119650 | A1 | 6/2005 | Sanders et al. ................ 424/426 | WO | 93/13816 | 7/1993 |
| 2005/0251134 | A1 | 11/2005 | Woloszko et al. ............... 606/32 | WO | 93/20747 | 10/1993 |
| 2005/0261754 | A1 | 11/2005 | Woloszko et al. ............... 606/32 | WO | 94/03134 | 2/1994 |
| 2005/0288665 | A1 | 12/2005 | Woloszko et al. ............... 606/41 | WO | 94/04220 | 3/1994 |
| 2006/0036237 | A1 | 2/2006 | Davison et al. ................. 606/41 | WO | 94/08654 | 4/1994 |
| 2006/0095031 | A1 | 5/2006 | Ormsby ......................... 606/34 | WO | 94/10924 | 5/1994 |
| 2006/0106379 | A1* | 5/2006 | O'Brien et al. ................. 606/45 | WO | 94/14383 | 7/1994 |
| 2006/0178670 | A1 | 8/2006 | Woloszko et al. ............... 606/48 | WO | 94/26228 | 11/1994 |
| 2006/0189971 | A1 | 8/2006 | Tasto et al. ..................... 606/32 | WO | 95/05780 | 3/1995 |
| 2006/0253117 | A1 | 11/2006 | Hovda et al. ................... 128/898 | WO | 95/05781 | 3/1995 |
| 2006/0259025 | A1 | 11/2006 | Dahla ........................... 607/108 | WO | 95/05867 | 3/1995 |
| 2007/0005051 | A1* | 1/2007 | Kampa ............................ 606/41 | WO | 95/10326 | 4/1995 |
| 2007/0010808 | A1 | 1/2007 | Dahla ............................. 606/41 | WO | 95/30373 | 11/1995 |
| 2007/0106288 | A1 | 5/2007 | Woloszko et al. ............... 606/41 | WO | 95/34259 | 12/1995 |
| 2007/0149966 | A1 | 6/2007 | Dahla et al. .................... 606/41 | WO | 96/00042 | 1/1996 |
| 2007/0161981 | A1 | 7/2007 | Sanders et al. .................. 606/41 | WO | 96/07360 | 3/1996 |
| 2007/0208334 | A1 | 9/2007 | Woloszko et al. ............... 606/41 | WO | 96/34568 | 11/1996 |
| 2007/0208335 | A1 | 9/2007 | Woloszko et al. ............... 606/41 | WO | 96/35469 | 11/1996 |
| 2007/0213700 | A1 | 9/2007 | Davison et al. ................. 606/32 | WO | 96/39914 | 12/1996 |
| 2007/0282323 | A1 | 12/2007 | Woloszko et al. ............... 606/41 | WO | 96/39962 | 12/1996 |
| 2008/0021447 | A1 | 1/2008 | Davison et al. ................. 606/41 | WO | 96/39964 | 12/1996 |
| 2008/0167645 | A1 | 7/2008 | Woloszko ....................... 606/40 | WO | 96/39965 | 12/1996 |
| 2008/0167646 | A1 | 7/2008 | Godara et al. .................. 606/41 | WO | 96/39967 | 12/1996 |
| 2008/0234673 | A1 | 9/2008 | Marion et al. .................. 606/45 | WO | 97/00646 | 1/1997 |
| 2008/0300590 | A1 | 12/2008 | Horne et al. .................... 606/35 | WO | 97/00647 | 1/1997 |
| 2009/0069807 | A1 | 3/2009 | Eggers et al. ................... 606/48 | WO | 97/15238 | 5/1997 |
| 2009/0138011 | A1 | 5/2009 | Epstein .......................... 606/42 | WO | 97/18765 | 5/1997 |
| 2009/0209958 | A1 | 8/2009 | Davison et al. ................. 606/41 | WO | 97/24073 | 7/1997 |
| 2010/0042095 | A1 | 2/2010 | Bigley et al. ................... 606/41 | WO | 97/24074 | 7/1997 |
| 2010/0152724 | A1 | 6/2010 | Marion et al. .................. 606/41 | WO | 97/24992 | 7/1997 |
| 2010/0204690 | A1 | 8/2010 | Bigley et al. ................... 606/41 | WO | 97/24993 | 7/1997 |
| 2011/0077643 | A1 | 3/2011 | Dahla et al. .................... 606/41 | WO | 97/24994 | 7/1997 |
| 2011/0270242 | A1 | 11/2011 | Marion .......................... 606/35 | WO | 97/25101 | 7/1997 |
| 2012/0179157 | A1 | 7/2012 | Frazier et al. ................... 606/41 | WO | 97/32551 | 9/1997 |
| | | | | WO | 97/33523 | 9/1997 |
| | | FOREIGN PATENT DOCUMENTS | | WO | 97/34540 | 9/1997 |
| DE | | 3930451 A1 | 3/1991 | WO | 97/41786 | 11/1997 |
| DE | | 4425015 | 1/1996 | WO | 97/44071 | 11/1997 |
| DE | | 296 09 350 | 8/1996 | WO | 97/48345 | 12/1997 |
| DE | | 195 37 084 | 4/1997 | WO | 97/48346 | 12/1997 |
| DE | | 296 19 029 | 4/1997 | WO | 98/07468 | 2/1998 |
| DE | | 19850671 | 5/1999 | WO | 98/14131 | 4/1998 |
| DE | | 10254668 | 6/2004 | WO | 98/17185 | 4/1998 |
| DE | | 69822877 | 1/2005 | WO | 98/17186 | 4/1998 |
| DE | | 202008000276 | 6/2008 | WO | 98/27877 | 7/1998 |
| DE | | 102009057921 A1 | 6/2010 | WO | 98/27879 | 7/1998 |
| EP | | 0 502 268 | 9/1992 | WO | 98/27880 | 7/1998 |
| EP | | 0 515 867 | 12/1992 | WO | 98/30144 | 7/1998 |
| EP | | 543123 | 5/1993 | WO | 98/34550 | 8/1998 |
| EP | | 0 597 463 | 5/1994 | WO | 98/34558 | 8/1998 |
| EP | | 774926 | 3/1995 | WO | 98/38925 | 9/1998 |
| EP | | 0 650 701 | 5/1995 | WO | 98/39038 | 9/1998 |
| EP | | 0703461 A2 | 3/1996 | WO | 99/00060 | 1/1999 |

| WO | 99/20185 | 4/1999 |
| WO | 99/42037 | 8/1999 |
| WO | 99/44506 | 9/1999 |
| WO | 99/51155 | 10/1999 |
| WO | 99/51158 | 10/1999 |
| WO | 00/09053 | 2/2000 |
| WO | 01/26570 | 4/2001 |
| WO | 01/87154 | 5/2001 |
| WO | 01/95819 | 12/2001 |
| WO | 02/36028 | 5/2002 |
| WO | 02/078557 | 10/2002 |
| WO | 03/024339 | 3/2003 |
| WO | 2005/125287 | 12/2005 |
| WO | 2008/073727 | 6/2008 |
| WO | 2009/094392 | 7/2009 |
| WO | 2011/071482 | 6/2011 |

OTHER PUBLICATIONS

EP Search Report for EP 04778347 4pgs, Feb. 22, 2011.
PCT International Search Report for PCT/US96/18505, 3 pgs, Mailed Jan. 17, 1997.
PCT Notif of the Int'l Search Report and Written Opinion for PCT/US09/67001 6 pgs, Mailed Jan. 29, 2010.
UK Search Report for GB0921635.9 3pgs, Apr. 12, 2010.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC—III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.

Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164 pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atheroscrotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop", Nov. 1989.

Valley Forge Scientific Corp., "Summary of Safety and Effective Information from 510K", 2pgs, 1991.

Valley Forge's New Products, CLINICA, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 2000.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endroscopic electrodes, and tissue," Gastrointestinal Endoscopy, vol. 38, No. 2, pp. 118-122, 1992.

Buchelt, et al. "Excimer Laser Ablation of Fibrocartilage: An In Vitro and In Vivo Study", Lasers in Surgery and Medicine, vol. 11, pp. 271-279, 1991.

Costello et al., "Nd: YAG Laser Ablation of the Prostate as a Treatment for Benign Prostatic Hypertrophy", Lasers in Surgery and Medicine, vol. 12, pp. 121-124, 1992.

Hardy et al., "Regional Myocardial Blood Flow and Cardiac mechanics in dog Hearts with CO2 laser-induced Intramyocardial Revascularization", Basic Research in cardiology 85:179-196, 1990.

Mirhoseini et al., "New Concepts in Revascularization of the Myocardium", Ann Thorac Surg 45:415-420 (1988).

Mirhoseini et al., "Revascularization of the heart by Laser", J. of Microsurgery 2:253-260 (1981).

Mirhoseini et al., "Transmyocardial Laser Revascularization: A Review", J. of Clinical Laser medicine & Surgery 11 (1) :15-19 (1993).

Mirhoseini et al., "Transventricular Revascularization by Laser", Lasers in Surgery and Medicine 2:187-198 (1982).

Rand et al., "Effect of Elecctrocautery on Fresh Human Articular Cartilage", J. Arthro. Surg., vol. 1, pp. 242-246, 1985.

Walter et al., "Treatment of Acute Myocardial Infarction by Transmural Blood Supply from the Ventricular Cavity", Erop. Surgery Res. 3:130-138 (1971).

Whittaker et al., "Transmural Channels Can Protect Ischemic Tissue", Circulation 93(1):143-152, Jan. 1, 1996.

EP Search Report for EP01124768 2 pgs, Nov. 30, 2001.

Ep Search Report for EP01935650 10 pgs, Mailed Jul. 26, 2006.

EP Search Report for EP01935650 8 pgs, Mailed May 3, 2005.

EP Search Report for EP02768969 3 pgs, Mailed Feb. 12, 2007.

EP Search Report for EP03762238 3 pgs, Mailed Jun. 2, 2006.

EP Search Report for EP94916716 2 pgs, Oct. 29, 1996.

EP Search Report for EP96941386 2 pgs, Nov. 27, 1998.

EP Search Report for EP98952032 2 pgs, Nov. 24, 2000.

EP Search Report for EP 03736488 3 pgs, Mailed Jun. 25, 2009.

PCT International Search Report for PCT/US00/07718 1 pg, Mailed Sep. 5, 2000.

PCT International Search Report for PCT/US01/16006 1 pg, Mailed Aug. 14, 2001.

PCT International Search Report for PCT/US02/31640 1 pg, Mailed May 23, 2003.

PCT International Search Report for PCT/US03/04689 1 pg, Mailed Sep. 26, 2003.

PCT International Search Report for PCT/US03/12790 1 pg, Mailed Aug. 12, 2003.

PCT International Search Report for PCT/US03/20574 1 pg, Mailed May 25, 2005.

PCT International Search Report for PCT/US04/22803 1 pg, Mailed Apr. 29, 2005.

PCT International Search Report for PCT/US05/07038 1 pg, Mailed Sep. 2, 2005.

PCT International Search Report for PCT/US94/05168 1 pg, Mailed Oct. 18, 1994.

PCT International Search Report for PCT/US98/20768 1 pg, Mailed Jan. 20, 1999.

PCT International Search Report for PCT/US98/22327 1 pg, Mailed Feb. 9, 1999.

PCT IPER for PCT/US01/16006 3pgs, Apr. 16, 2002.

PCT IPER for PCT/US98/22327 4pgs, Aug. 27, 2000.

PCT Written Opinion for PCT/US04/22803 3pgs, Mailed Apr. 29, 2005.

PCT Written Opinion for PCT/US05/07038 3pgs, Mailed Sep. 2, 2005.

UK Search Report for GB0805061.9 1 pg, Jul. 15, 2008.

UK Search Report for GB1106425.0 6 pages, Mailed Aug. 16, 2011.

UK combined Search and Examination Report for GB1121048.1 3pgs, Apr. 18, 2012.

* cited by examiner

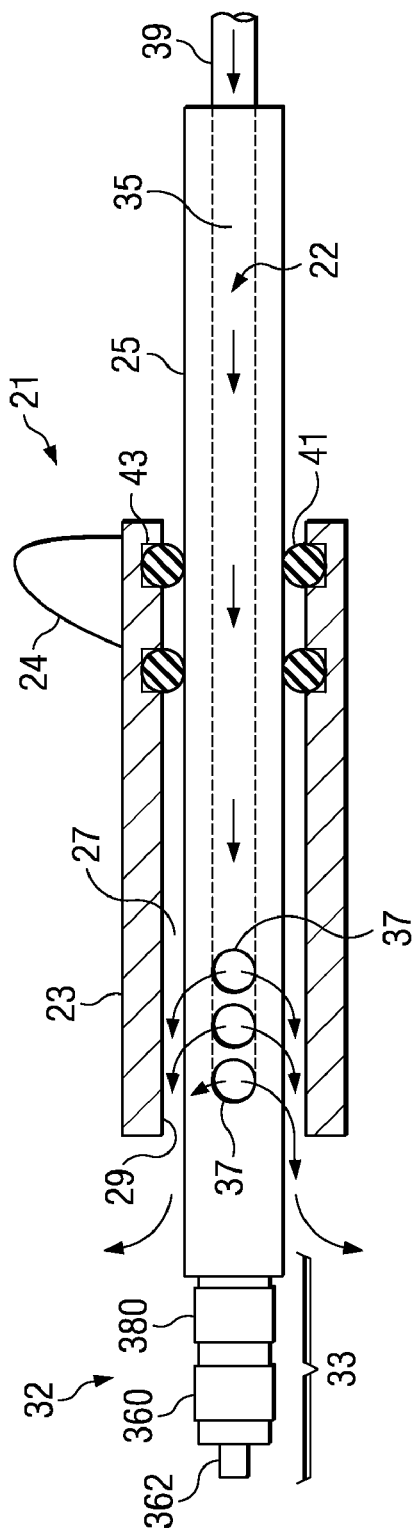
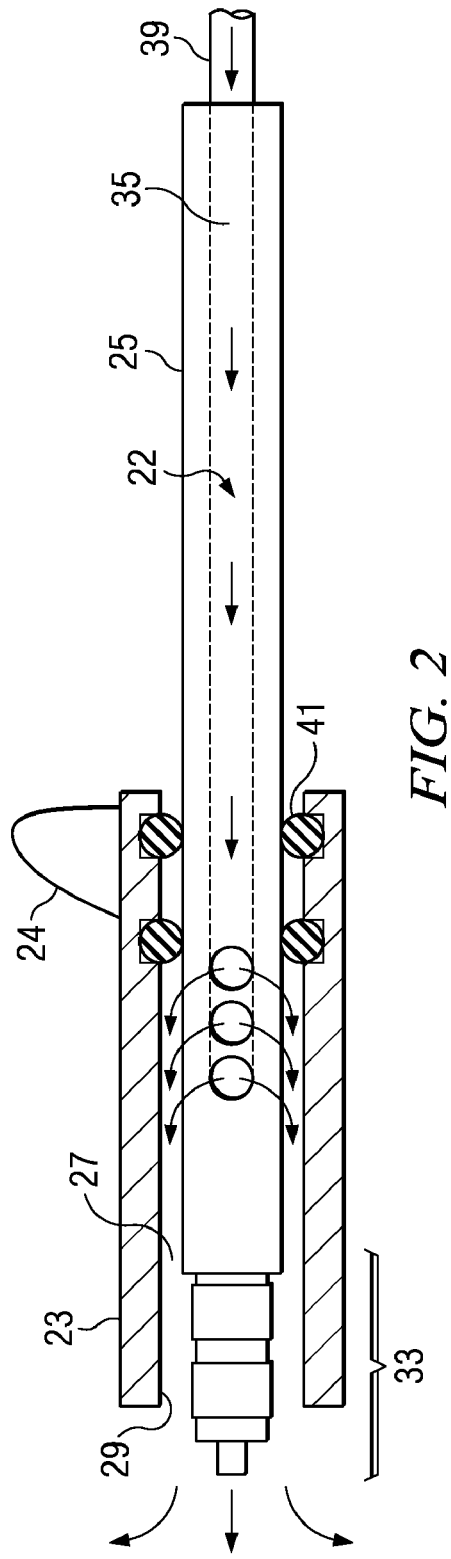
FIG. 1
FIG. 2

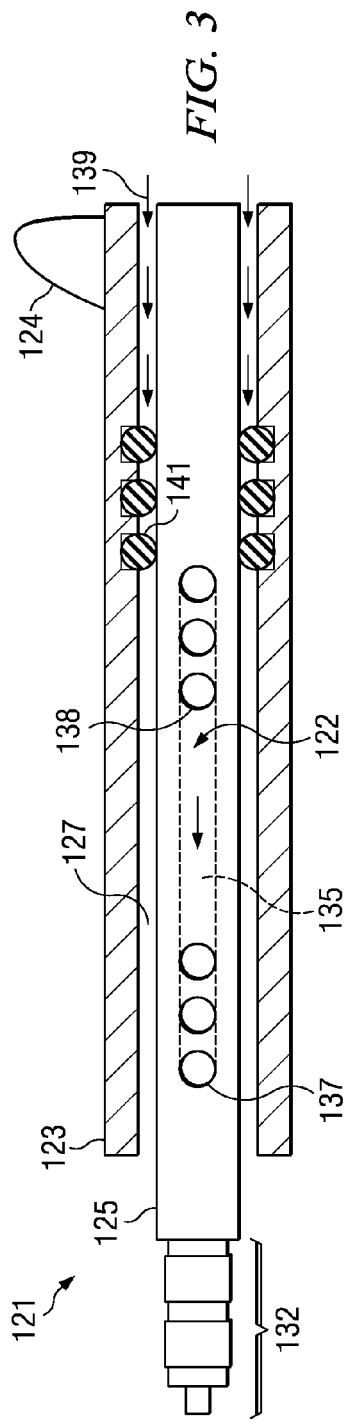
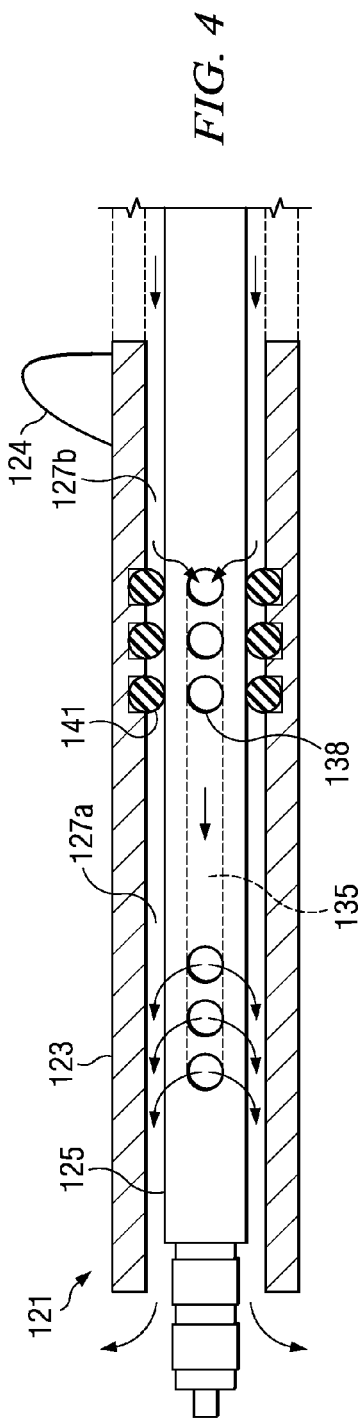
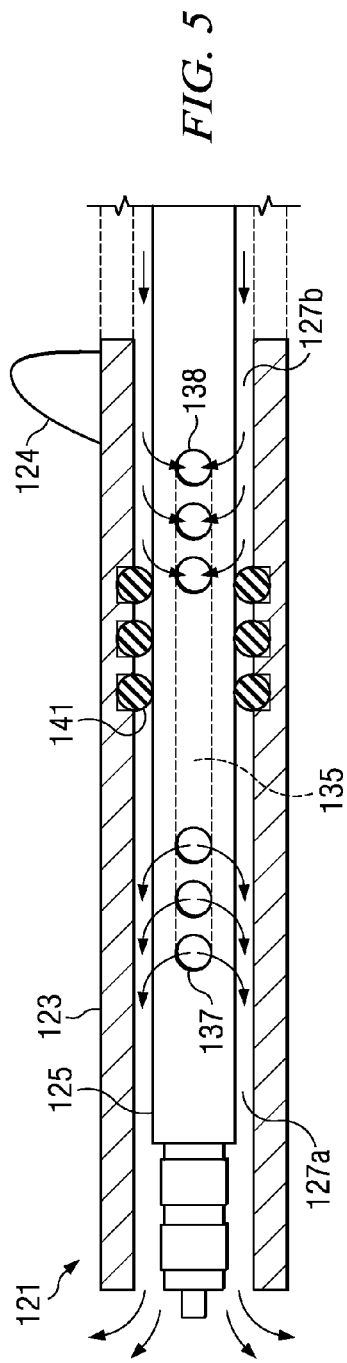

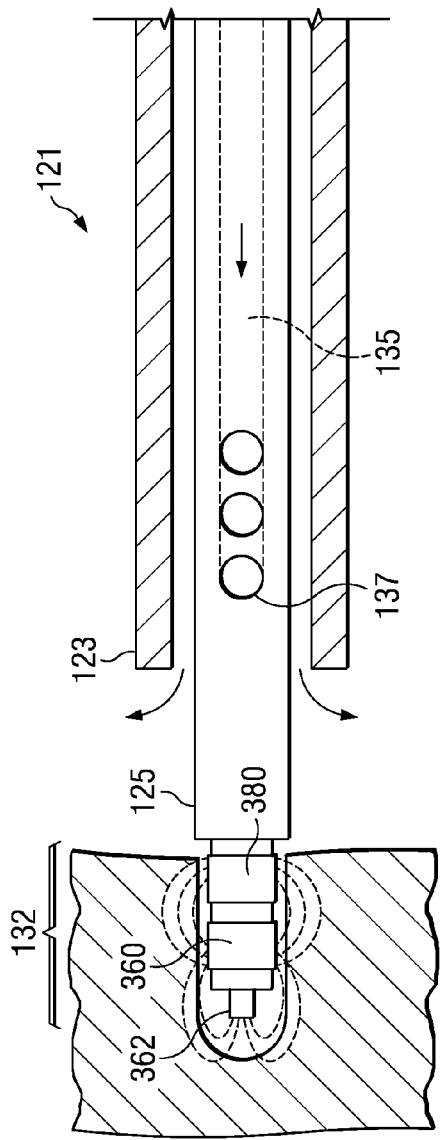
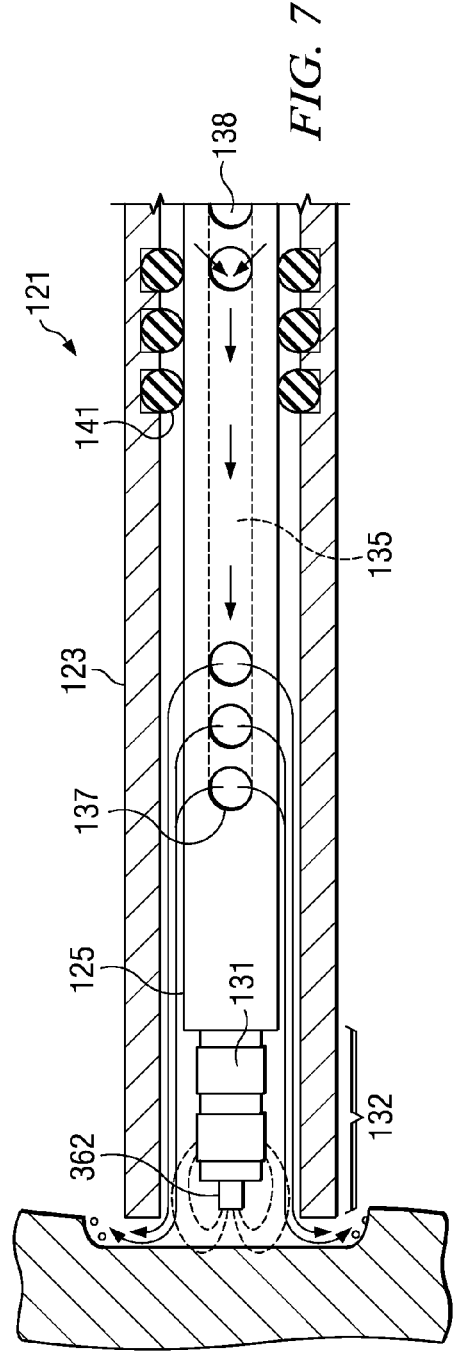

SYSTEM, METHOD AND APPARATUS FOR ELECTROSURGICAL INSTRUMENT WITH MOVABLE FLUID DELIVERY SHEATH

TECHNICAL FIELD

The present disclosure relates in general to electrosurgical instruments and, in particular, to an electrosurgical instrument with a fluid delivery device for controllably supplying fluid to a treatment site. More particularly, the present disclosure relates to a system, method and apparatus for an electrosurgical instrument having active and return electrodes with a movable fluid delivery sheath for variable fluid supply during surgical procedures.

DESCRIPTION OF THE RELATED ART

In some electrosurgical procedures an instrument (see, e.g., U.S. Pat. Nos. 5,683,366 and 6,235,020, which are incorporated herein by reference) has an active electrode and a return electrode that are used to treat body tissue. Treatment with this instrument may include, for example, coagulation, cutting, ablating, abrading or puncturing the tissue. In various designs, a current path is created between the active and return electrodes, thereby generating a limited plasma field between the electrodes and applying the plasma to the tissue, preferably without passing the current through the tissue. The current path may be created by providing an electrically conductive fluid at the target, or in some instances immersing the target site within electrically conductive fluid. It is preferred that the electrically conductive fluid has sufficient conductivity such that the fluid is ionized when subject to sufficient radio frequency (RF) electrical energy to thereby form the limited plasma. The conductive fluid path is an electrolyte, such as saline, lactated ringers solution, or conductive gels. One of the electrodes, referred to as the active electrode, is designed to generate a higher current density relative to other electrode, which is referred to as the return electrode. The source of the current is a high frequency voltage applied across the electrodes.

In some electrosurgical procedures an electrosurgical instrument (see, e.g., U.S. Pat. Nos. 6,159,208, 6,203,542 6,432,103 and 6,544,261 which are incorporated herein by reference) has at least two active electrode including at least one ablation electrode, at least one coagulation electrode and a return electrode that is used to treat body tissue and more particularly these instruments are operable to create a channel or hole into the target tissue. The present disclosure may include an instrument that is capable of performing a channeling technique in which small holes or channels are formed within tissue structures in the mouth, such as the tonsils, tongue, palate and uvula, and thermal energy is applied to the tissue surface immediately surrounding these holes or channels to cause thermal damage to the tissue surface, thereby stiffening the surrounding tissue structure. Applicant has discovered that such stiffening of certain tissue structures in the mouth and throat helps to prevent the tissue structure from obstructing the patient's upper airway during sleep. It is preferred that an electrically conductive fluid has sufficient conductivity such that the fluid is ionized when subject to sufficient radio frequency (RF) electrical energy to thereby form a limited plasma during use of the channeling instrument described above.

Although separate or additional fluid delivery systems may be employed for such applications described above, they add significant cost and complication to such procedures, while requiring multiple fluid delivery lines and crowding of the surgical area. Thus, an improved solution that overcomes the limitations of the prior art would be desirable.

BRIEF SUMMARY OF THE INVENTION

Embodiments of a system, method, and apparatus for an electrosurgical instrument having at least one active and at least one return electrode with a movable fluid delivery sheath for variable fluid supply during surgical procedures are disclosed. The electrosurgical fluid delivery apparatus has an outer sheath that is external to a shaft to provide an annular fluid delivery channel or lumen. The sheath assembly is axially slidable and movable relative to the fluid delivery element between first and second positions for treating the target site and controllable fluid delivery, respectively. The first position comprises positioning the distal leading edge of the sheath assembly axially proximal to the electrode assembly. The second position may comprise positioning the distal leading edge of the sheath assembly axially adjacent to the distal end of the shaft, or axially distal to the distal end of the shaft.

The fluid delivery element comprises an inner lumen extending through a portion of the shaft, and at least one port extending radially through the shaft. The at least one port is in fluid communication with the inner lumen. A fluid source may be connected to the inner lumen for providing fluid through the inner lumen and port. In one embodiment, the sheath assembly comprises a tube that is slidably movable relative to and concentric with the shaft. The tube defines an annular space or outer lumen between the tube and the shaft and has a radial seal. The radial seal is disposed between an outer surface of the shaft and an inner surface of the tube and sealingly engages the shaft and the tube.

In another embodiment, the sheath assembly has a range of motion between the first and second positions that provides a variable level of fluid delivery in the vicinity of the electrode assembly. Preferably, the sheath assembly is movable to provide a minimal level of fluid delivery proximate the electrode assembly in the first position, to a maximum level of fluid delivery adjacent to the electrode assembly in the second position. The fluid delivery element comprises an inner lumen extending through a portion of the shaft, and first and second plurality of ports extending radially through the shaft in fluid communication with the inner lumen. The first and second plurality of ports are preferably axially spaced apart. A fluid source may be connected to the outer lumen proximal to the radial seal. When the sheath assembly is in an intermediate or second position, the fluid source may provide a sequential fluid path through the outer lumen that is proximal to the radial seal, the first plurality of ports, to the second plurality of ports via the inner lumen and finally out through the outer lumen that is distal to the radial seal.

This disclosure may further comprise a method for treating tissue including the steps of positioning an active electrode adjacent to tissue and positioning a sheath assembly in a first position. The first position creates a delivery region that is proximal to the active electrode. A first high frequency voltage is then applied between the active electrode and a return electrode, and while this voltage is being applied, fluid may be delivered to the region proximal to the active electrode. The sheath assembly may then be advanced to a second position, the second position creating a fluid delivery region adjacent to the active electrode. A second high frequency voltage between the first active electrode and return electrode is then applied while delivering fluid to the region adjacent to the active electrode. The first and the second voltages levels may be substantially similar.

This disclosure may further comprise a method for creating a channel into tissue including the steps of positioning an electrode assembly comprising a first active electrode, a return electrode and a coagulation electrode adjacent to the target tissue. A sheath assembly is then retracted, the sheath assembly being disposed adjacent to a fluid delivery element, and wherein the retracting step may provide at least a portion of electrically conductive fluid at a position axially spaced away from the first active electrode. A first high frequency voltage is then applied between the first active electrode and the return electrode and during at least a portion of the applying step, the active electrode is advanced into the tissue, thereby creating a channel or hole in the tissue. At the same time or sequential to applying the first voltage, a second high frequency voltage may also be applied between the return electrode and the coagulation electrode. The electrode assembly may then be retracted from the channel and the sheath assembly may be advanced so as to provide at least a portion of the electrically conductive fluid at a position adjacent to the electrode assembly. A third high frequency may then be applied between the first active electrode and the return electrode to ablate the surface of the tissue. The first, second and third high frequency levels may all be substantially similar.

The foregoing and other objects and advantages of the present disclosure will be apparent to those skilled in the art, in view of the following detailed description of the present invention, taken in conjunction with the appended claims and the accompanying drawings.

BRIEF DESCRIPTION OF THE DRAWINGS

So that the manner in which the features and advantages of the present disclosure are attained and can be understood in more detail, a more particular description of the apparatus and methods briefly summarized above may be had by reference to the embodiments thereof that are illustrated in the appended drawings. However, the drawings illustrate only some embodiments of this disclosure and therefore are not to be considered limiting of its scope as the disclosure may admit to other equally effective embodiments.

FIG. 1 is a sectional side view of one embodiment of an electrosurgical instrument shown in a first position and is constructed according to the teachings of the present disclosure;

FIG. 2 is a sectional side view of the electrosurgical instrument of FIG. 1, shown in a second position, and is constructed according to the teachings of the present disclosure;

FIGS. 3-5 are sectional side views of another embodiment of an electrosurgical instrument shown in three different positions and is constructed according to the teachings of the present disclosure;

FIGS. 6 and 7 are enlarged schematic sectional side views of the electrosurgical instrument of FIGS. 3-5 in operation and is constructed according to the teachings of the present disclosure;

DETAILED DESCRIPTION

Figure 8:
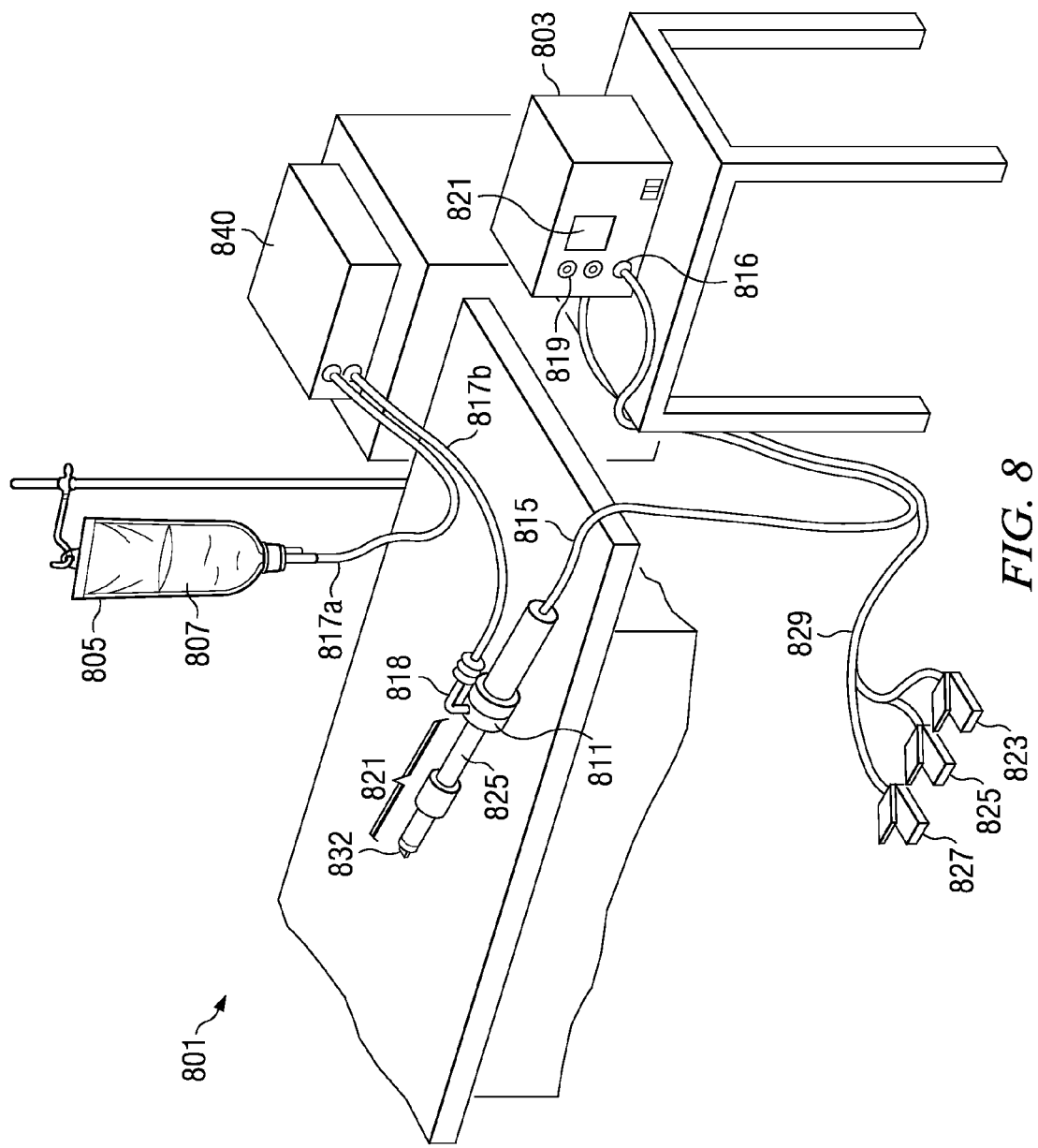
FIG. 8 is a schematic diagram of one embodiment of a system for operating an electrosurgical instrument and is constructed according to the teachings of the present disclosure.

Before the present disclosure is described in detail, it is to be understood that this is not limited to particular variations set forth herein as various changes or modifications may be made to the disclosure described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application. Nothing herein is to be construed as an admission that the present is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present disclosure may have a variety of configurations as described above. However, one variation employs a treatment device using Coblation® technology.

As stated above, the assignee of the present disclosure developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882 the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032, 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the present disclosure, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use according to the present disclosure may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one second interval that energy is applied) is on the order of about 50% for the present disclosure, as compared with pulsed lasers which typically have a duty cycle of about 0.0001%.

The preferred power source of the present disclosure delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Referring now to FIGS. 1-8, embodiments of a system, method and apparatus for an electrosurgical instrument having at least one active electrode and a return electrode with a movable fluid delivery sheath for variable fluid delivery during surgical procedures are disclosed. FIGS. 1 and 2 illustrate one embodiment of an electrosurgical fluid delivery apparatus 21 having an outer sheath 23 and grip 24 that is external to an instrument shaft 25 to provide an annular fluid delivery channel 27 or lumen. The distal terminus 29 of outer sheath 23 defines an annular fluid egress at a moveable location relative to electrode assembly 32. In FIG. 1 distal terminal or distal leading edge 29 is shown proximal to electrode assembly 32.

The direction of flow of fluid during use of apparatus 21 is indicated by the arrows. Electrically conductive fluid supplied to the distal end of apparatus 21 forms a current flow path between active electrodes 362 or 380 and return electrode 360, and may facilitate generation of plasma in the vicinity of active electrodes 362 or 380, as described hereinabove. Provision of an electrically conductive fluid may be particularly valuable in a dry field situation (e.g., in situations where there is a paucity of native electrically conductive bodily fluids, such as blood, synovial fluid, etc.). The electrically conductive fluid may be aspirated or removed from the distal end of apparatus 21 by a separate device (not shown).

The fluid delivery apparatus 21 may deliver fluid to a target site. For example, during an electrosurgical ablative procedure, it may be desirable to deliver electrically conductive fluid, to the target site to control the rate of ablation. It may also be desirable not only to control the rate of fluid delivery but also the location or dispersion level of the fluid delivery relative to the tissue treatment site. For example, it may be desirably to have the fluid delivery directed closer to the tissue treatment site (as shown in FIG. 2.) or alternatively dispersed around the tissue target site area (as shown in FIG. 1). As described more so in the description above, the tissue effect and efficacy of any vapor layer may be altered by many factors, including but not limited to the quantity of fluid supplied but also the location or dispersion level of the fluid relative to the treatment site.

The outer sheath 23, or sheath assembly, may be disposed adjacent to the fluid delivery element 22. The sheath assembly 23 is axially movable relative to the fluid delivery element 22 between a first position (FIG. 1) for treating the target site with minimal fluid delivery which may be dispersed further away from the target site and a second position (FIG. 2) for increased fluid delivery, where the fluid may also be directed closer to the target site. The first position may comprise positioning a distal leading edge 29 of the sheath assembly 23 axially proximal to the electrode assembly 32 or the distal end portion 33 of the shaft 25. The second position may comprise positioning the distal leading edge 29 of the sheath assembly 23 axially adjacent to the distal end portion 33 of the shaft 25, or alternatively axially distal to the distal end portion 33 of the shaft 25.

The fluid delivery element 22 may comprise an inner lumen 35 extending through a portion of the shaft 25, and at least one port 37 (e.g., three shown) extending radially through the shaft 25. The port(s) 37 are in fluid communication with the inner lumen 35 as well as outer lumen 27, thereby creating a fluid delivery path in the annular space surrounding shaft 25 and defined by sheath assembly 23 and seals 41. A conductive fluid source 39 (shown schematically) is connected to the inner lumen 35 for providing fluid though inner lumen 35, though the port(s) 37 and via outer lumen 27 to the egress located at distal leading edge 29. The port 37 may comprise a plurality of ports that are located adjacent or slightly proximal to the distal end portion 33 of the shaft 25 and axially spaced from the electrode assembly 32.

In one embodiment, the sheath assembly 23 comprises a tube that is slidably movable relative to and concentric with the shaft 25. Grip 24 may be disposed on sheath assembly 23 in certain embodiments to provide an ergonomic interface for the user (e.g., with the user's finger) in order to ease movement and sliding of sheath assembly 23. The sheath 23 defines an annular space or outer lumen 27 between the tube and the shaft 25 and has at least one radial seal 41. The radial seal 41 is disposed between an outer surface of the shaft 25 and an inner surface of the sheath 23 and sealingly engages the shaft 25 and the sheath 23. The radial seal 41 may comprise a plurality of o-rings that are seated in an axial series of radial grooves 43 formed in the inner surface of the sheath 23, with the radial grooves 43 being axially spaced from each other.

In the first position illustrated in FIG. 1, sheath assembly 23 is positioned to create a relatively low rate of fluid delivery in proximity to the target site and the area in the vicinity of the electrode assembly 32. In this first position, minimal fluid is delivered to the electrode assembly area 32, as it disperses away from the target area and a less effective vapor layer may be formed around the electrode assembly 32. Sheath assembly 23 may be deployed in the first position illustrated in FIG. 1 if the user detects the ablative effect on the target tissue is too intense, as the decreased fluid delivery may mitigate the efficacy of the vapor layer and plasma formed at electrode assembly 32. Alternatively, in the second position illustrated in FIG. 2, edge 29 of sheath assembly 23 is positioned adjacent to or distal to electrode assembly 32 to create a larger fluid delivery field and a relatively higher delivery rate directed to the target site and in the vicinity of electrode assembly 32. In this second position, sheath assembly 23 is deployed for a considerable rate of delivery, to create a more effective vapor layer and potentially a more efficient tissue ablation.

Electrode assembly 32 illustrates an electrode assembly embodiment often used for forming holes or channels in the tissues such as turbinates, soft palate tissue, tongue or tonsils, with the methods described in detail below. Namely, a high frequency voltage difference is applied between active and return electrodes 362, 360, respectively, in the presence of an electrically conductive fluid such that an electric current passes from the active electrode 362, through the conductive fluid, to the return electrode 360. The voltage is sufficient to vaporize the fluid around active electrode assembly 32 to form a plasma with sufficient energy to effect molecular dissociation of the tissue. The distal end portion 33 is then axially advanced through the tissue as the tissue is removed by the plasma in front of the end portion 33. It may be desired in some procedures to increase the thermal damage caused to the tissue surrounding hole or channel to coagulate any blood vessels exposed during channeling. Electrical current is therefore then passed through coagulation electrode 380 and return electrodes 360, which both have relatively large, smooth exposed surfaces to minimize high current densities at their surfaces, which minimizes damage to the surface of hole or channel.

Referring now to the embodiments of FIGS. 3-7, instrument 121 including sheath assembly 123 may be provided with a range of motion between the first and second positions that provides a variable level of fluid delivery at variable dispersion levels. Sheath assembly 123 is preferably slidable between a first deployed position where a minimal level of fluid delivery occurs (FIGS. 3 and 6), to a second deployed position where a maximum level of fluid delivery (FIGS. 5 and 7). An intermediate level of fluid delivery is depicted in FIG. 4.

In these embodiments, the fluid delivery element 122 comprises an inner lumen 135 extending through a portion of the shaft 125, and may terminate at the distal port 137. First and second ports, 137 and 138 extend radially through the shaft 125 in fluid communication with the inner lumen 135. The first and second ports, 137 and 138 are located on or adjacent to opposite axial ends of the inner lumen 135. The sheath assembly 123 comprises a tube that is slidably movable relative to and concentric with the shaft 125. Grip 124 may be disposed on sheath assembly 123 in certain embodiments to provide an ergonomic interface for the user (e.g., with the user's finger) in order to ease movement and sliding of sheath assembly 123. The sheath 123 defines an annular space or outer lumen 127 between the sheath 123 and the shaft 125 and has at least one radial seal 141. The radial seal 141 is disposed in the outer lumen 127 between an outer surface of the shaft 125 and an inner surface of the sheath 123 and sealingly engages the shaft 125 and the tube 123.

A fluid source 139 (e.g., indicated schematically) is connected to the outer lumen 127b proximal to the radial seal 141. Referring now to FIG. 3, sheath assembly 123 is deployed such that seals 141 are disposed proximally of both the first and second ports 137, 138. In this configuration, no fluid delivery chamber is formed in the annular space between sheath assembly 123 and shaft 125 and distal seals 141, such that fluid delivery may be minimal. In this configuration, first and second ports, 137 and 138 are at the same pressure with no net fluid flow therebetween and thereby fluidly bypassed by way of seals 141 isolating the first and second ports, 137 and 138 from the fluid delivery chamber and the portion of outer lumen 127 connected to fluid source 139. When the sheath assembly 123 is in the intermediate position (FIG. 4) or in the second position (FIGS. 5 and 7), the fluid source 139 provides a sequential fluid delivery path through outer lumen 127b, proximal to seals 141, proximal ports 138, inner lumen 135, distal ports 137 and outer lumen 127a that is distal to the radial seal 141.

In the first position illustrated in FIGS. 3 and 6, sheath assembly 123 is positioned to create a relatively low rate of fluid delivery through inner lumen 135 to the target site and the area in the vicinity of the electrode terminal. Additionally, the relatively low fluid delivery rate in the vicinity of electrode assembly 132 inhibits the formation of an effective vapor layer and more efficient plasma for tissue treatment and ablation. Alternatively, in the second position illustrated in FIGS. 5 and 7, a distal edge of sheath assembly 123 is positioned adjacent to or distal to electrodes assembly 132 and in proximity to the target site to create more fluid being delivered to the target site and in vicinity of electrode assembly 132. As such, sheath assembly 123 is deployed for a considerable rate of fluid delivery and to focus the delivery of fluid to the target site and adjacent to electrode assembly 132. Further, sheath assembly 123 may be deployed in the second position illustrated in FIGS. 5 and 7 if the user detects the ablative effect on the target tissue is not sufficiently intense, as the increased fluid may improve the efficacy of the vapor layer and plasma formed at electrode assembly 132.

FIG. 6 also shows a schematic example of the electrode assembly 132 channeling into tissue. Sheath 123 is in the first position, so as to provide minimal fluid delivery in proximity to the electrode assembly 132. During channeling, ablative active electrode 362 may be used to create the channeling effect and coagulation electrode 380 may be activated to coagulate any blood vessels (not shown here) exposed during ablation. FIG. 7 shows a schematic of an electrosurgical instrument 121 treating target tissue at the tissue surface. The user may chose to apply energy through only one active electrode 362 as shown in this example.

Referring now to FIG. 8, an exemplary electrosurgical system 801 for treatment of tissue in "dry fields" is shown. System 801 also may be used in a "wet field," i.e., the target site is immersed in electrically conductive fluid. However, this system is particularly useful in dry fields where the fluid is preferably delivered through an electrosurgical probe 821 to the target site. As shown, electrosurgical system 801 generally comprises an electrosurgical hand piece or probe 821 connected to a power supply 803 for providing high frequency voltage to a target site and a fluid source 805 for supplying electrically conductive fluid 807 to probe 821. In addition, electrosurgical system 801 may include an endoscope (not shown) with a fiber optic head light for viewing the surgical site, particularly in sinus procedures or procedures in the ear or the back of the mouth. The endoscope may be integral with probe 821, or it may be part of a separate instrument. A fluid aspirator (not shown) may also be used to aspirate any fluid away from the surgical site.

As shown, probe 821 generally includes a proximal handle 811 and an elongate shaft 825 having an electrode assembly 832 at its distal end. A connecting cable 815 has a connector 816 for electrically coupling the electrodes assembly 832 to power supply 803. The electrode assembly 832 comprises at least two electrodes, that are electrically isolated from each other and each of the terminals is connected to an active or passive control network within power supply 803 by means of a plurality of individually insulated conductors (not shown). A fluid supply tube 817a may be connected to a fluid pump 840 which is then connected to fluid tube 818 via fluid supply tube 817b for supplying electrically conductive fluid 807 to the target site. Fluid tube 818 is fluidly coupled with an inner lumen (not shown here) of probe 821. Fluid pump 840 may comprise a positive displacement pump such as, for example, a peristaltic pump. The system 801 may also include a vacuum source as described herein that is coupled to a separate suction lumen or external tube for aspirating fluid from the target site. This suction lumen is not shown here.

Power supply 803 may comprise an operator controllable voltage level adjustment 819 to change the applied voltage level, which is observable at a voltage level display 821. Power supply 803 also includes first, second and third foot pedals 823, 825, 827 and a cable 829 that is removably coupled to power supply 803. The foot pedals 823, 825, 827 allow the surgeon to remotely adjust the energy level applied to electrode assembly 832. In an exemplary embodiment, first foot pedal 823 is used to place the power supply into the ablation mode and second foot pedal 825 places power supply 803 into the "coagulation" mode. The third foot pedal 827 allows the user to adjust the voltage level within the "ablation" mode.

In the ablation mode, a sufficient voltage is applied to the active electrodes to establish the requisite conditions for molecular dissociation of the tissue (i.e., vaporizing a portion of the electrically conductive fluid, ionizing charged particles within the vapor layer, and accelerating these charged particles against the tissue). As discussed above, the requisite voltage level for ablation will vary depending on the number, size, shape and spacing of the electrodes, the distance to which the electrodes extend from the support member, etc. Once the surgeon places the power supply in the ablation mode, voltage level adjustment 819 or third foot pedal 827 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 803 applies a low enough voltage to the active electrodes (or the coagulation electrode) to avoid vaporization of the electrically conductive fluid and subsequent molecular dissociation of the tissue. The surgeon may automatically toggle the power supply between the ablation and coagulation modes by alternately stepping on foot pedals 823, 825, respectively. This allows the surgeon to quickly move between coagulation and ablation in situ, without having to remove his/her concentration from the surgical field or without having to request an assistant to switch the power supply.

By way of example, as the surgeon is sculpting soft tissue in the ablation mode, the probe typically may simultaneously seal and/or coagulate small severed vessels within the tissue. However, larger vessels, or vessels with high fluid pressures (e.g., arterial vessels) may not be sealed in the ablation mode. Accordingly, the surgeon can simply actuate foot pedal 825, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by actuating foot pedal 823.

Figure 9:
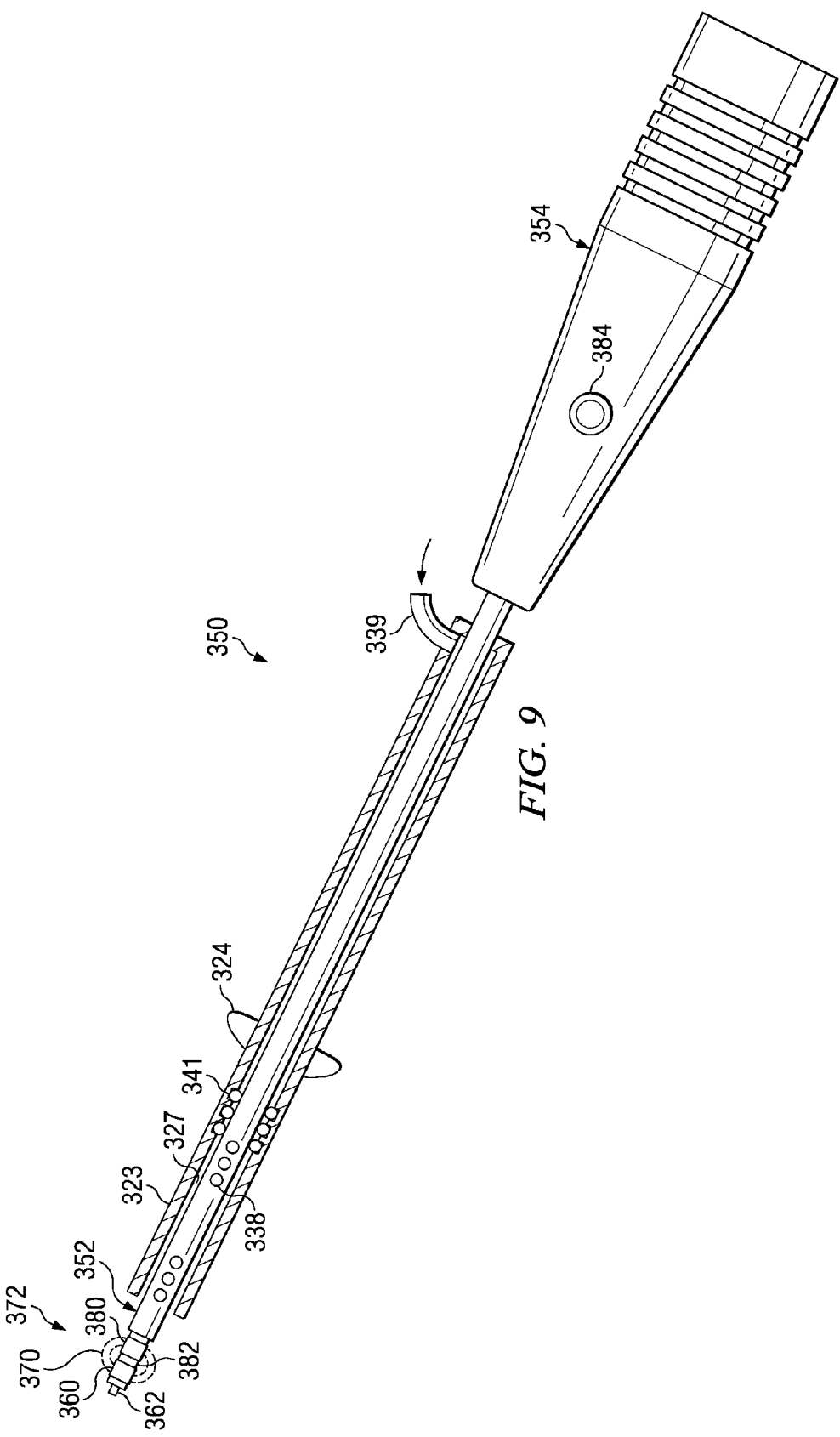
FIG. 9 is a side view of one embodiment of an electrosurgical instrument, constructed according to the teachings of the present disclosure.

FIG. 9 illustrates an embodiment of electrosurgical probe 350 incorporating an electrode assembly 372 having one or more active electrode(s) 362 and a proximally spaced return electrode 360. Return electrode 360 is typically spaced about 0.5 to 25 mm, preferably 1.0 to 5.0 mm from the active electrode(s) 362, and has an exposed length of about 1 to 20 mm. In addition, electrode assembly 372 may include a second active electrode 380 separated from return electrode 360 by an electrically insulating spacer 382. In this embodiment, handle 354 includes a switch 384 for toggling probe 350 between at least two different modes, an ablation mode and a subablation or thermal heating mode. In the ablation mode, voltage is applied between active electrode(s) 362 and return electrode 360 in the presence of some electrically conductive fluid, as described above. In the ablation mode, electrode 380 is deactivated. In the thermal heating or coagulation mode, active electrode(s) 362 may be deactivated and a voltage difference is applied between electrode 380 and electrode 360 such that a high frequency current 370 flows therebetween. Alternatively, active electrode(s) 362 may not be deactivated as the higher resistance of the smaller electrodes may automatically send the electric current to electrode 380 without having to physically decouple electrode(s) 362 from the circuit. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 380.

Sheath assembly 323 is shown in a first position, wherein the fluid delivery region is proximal to the electrode assembly 372 and wherein minimal fluid is being delivered to the electrode assembly 372. Sheath 323 may be adjusted to alternate positions using grip 324, so as to deliver more fluid in alternate locations. A fluid source 339 (e.g., indicated schematically) is connected to the outer lumen 327, and in this first position shown in FIG. 9, minimal fluid may travel through lumen 327 due to the relative positions of the seals 341 and ports 338.

Figure 10:
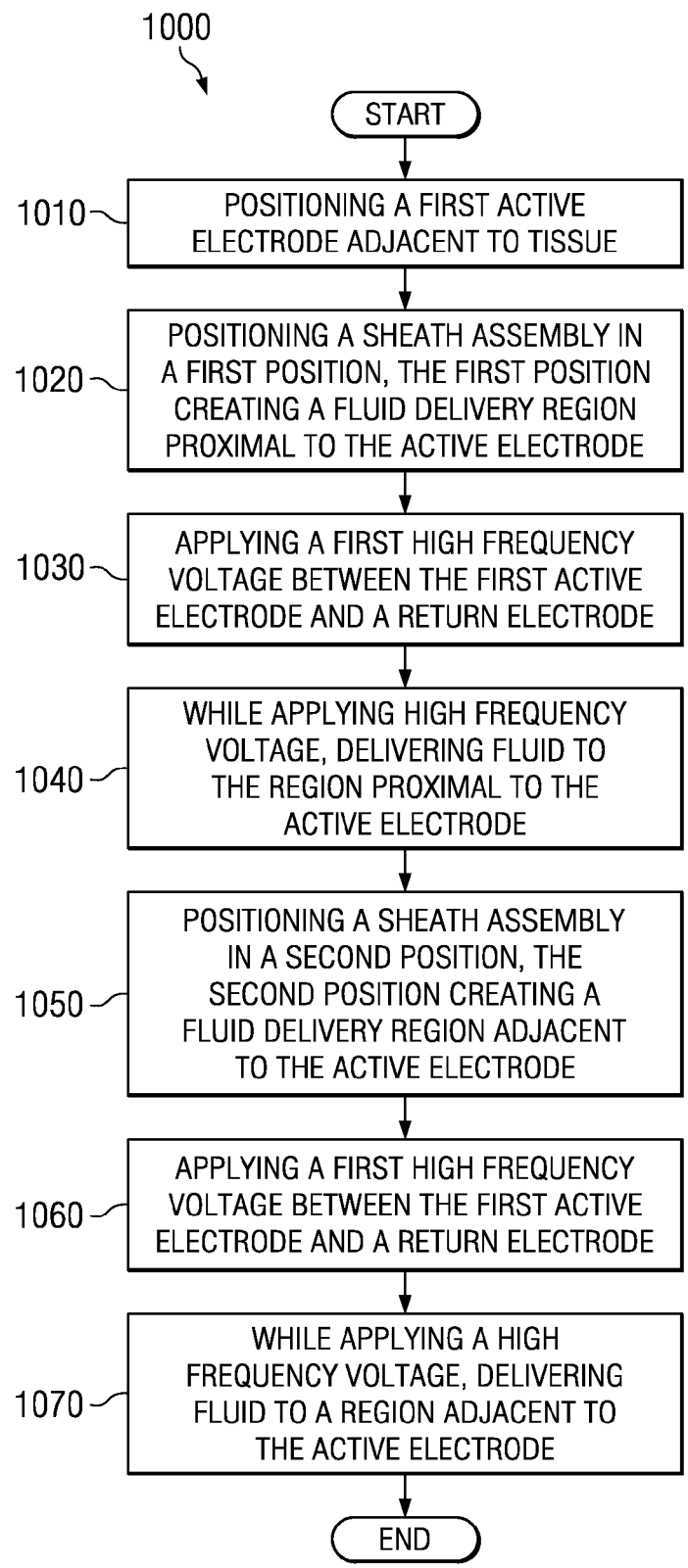
FIG. 10 shows a method of using an electrosurgical instrument embodiment described in the present disclosure.

Referring now to FIG. 10, a method (1000) for treating tissue in accordance with at least some of the embodiments described herein is illustrated, including the steps of: positioning a first active electrode adjacent to tissue (1010); positioning a sheath assembly in a first position, the first position creating an fluid delivery region proximal to the first active electrode (1020); applying a first high frequency voltage between the first active electrode and a return electrode (1030); while applying the first high frequency voltage, delivering fluid to the region proximal to the first active electrode (1040); positioning the sheath assembly in a second position, the second position creating a delivery region adjacent to the active electrode (1050); applying a second high frequency voltage between the first active electrode and a return electrode (1060); while applying the second high frequency voltage, delivering fluid to the region adjacent to the active electrode (1070).

Figure 11:
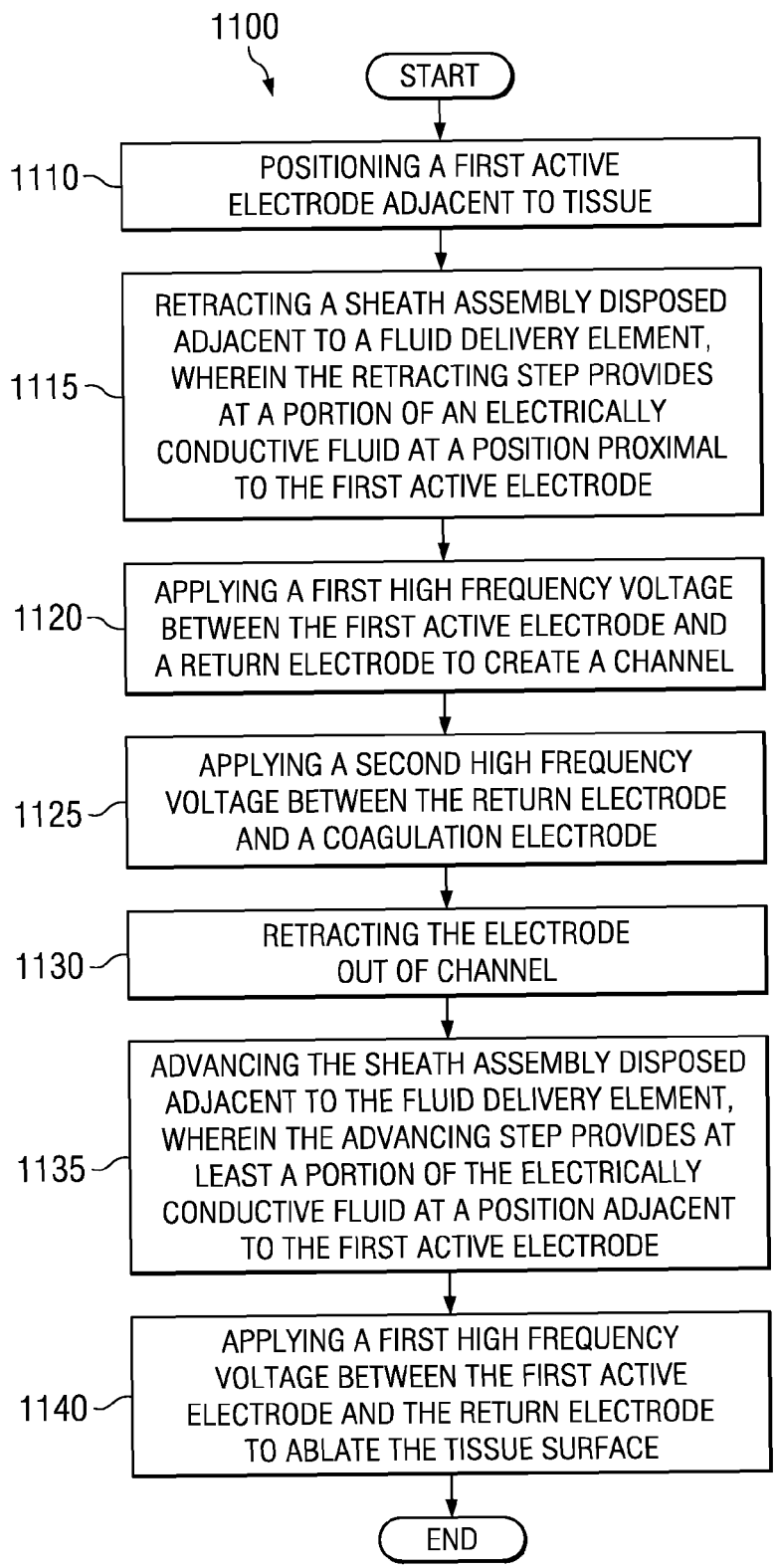
FIG. 11 shows a method of channeling into tissue in accordance with at least some embodiments.

Referring now to FIG. 11, a method 1100 for creating a channel into tissue in accordance with at least some of the embodiments described herein is illustrated, including the steps of: positioning an electrode assembly comprising a first active electrode, a return electrode and a coagulation electrode adjacent to tissue (1110); retracting a sheath assembly disposed adjacent to a fluid delivery element, wherein the retracting step delivers at least a portion of electrically conductive fluid at a position axially spaced away from the first active electrode (1115); applying a first high frequency voltage between the first active electrode and the return electrode; during at least a portion of the applying step, advancing the active electrode into the tissue to create a channel (1120); applying a second high frequency voltage between the return electrode and coagulation electrode (1125); retracting the electrode assembly out of the channel (1130); advancing the sheath assembly disposed adjacent to the fluid delivery element, wherein the advancing step delivers at least a portion of the electrically conductive fluid at a position adjacent to the first active electrode (1035); and applying a high frequency between the first active electrode and the return electrode to ablate the surface of the tissue (1040).

While the invention has been shown or described in only some of its forms, it should be apparent to those skilled in the art that it is not so limited, but is susceptible to various changes without departing from the scope of the invention.

We claim:

1. A system for treating tissue, comprising:
an electrosurgical instrument having a shaft with a proximal end and a distal end portion;
an electrode assembly positioned on the distal end portion of the shaft comprising at least one active electrode and at least one return electrode axially spaced from the at least one active electrode;
a fluid delivery element for delivering electrically conductive fluid to the active electrode comprising an inner lumen extending through a portion of the shaft, and first and second ports extending radially through the shaft in fluid communication with the inner lumen; and
a sheath assembly disposed adjacently to the fluid delivery element and comprising at least one radial seal to sealingly engage the shaft and the sheath assembly, the sheath assembly being axially moveable relative to the fluid delivery element from a first position to a second position;
wherein the fluid delivery element further comprises a fluid source connected to the sheath assembly proximal to the at least one radial seal and, when the sheath assembly is in the second position, the fluid source flows through a sequential fluid delivery path, through the sheath assembly proximal to the at least one radial seal, the first port, the inner lumen, the second port, the sheath assembly that is distal to the radial seal and via a distal opening disposed adjacent the electrode assembly.

2. A system according to claim 1, wherein a distal leading edge of the sheath assembly is spaced axially proximal from the distal end portion of the shaft when the sheath assembly is in the first position, and the distal leading edge of the sheath assembly is disposed substantially axially adjacent to the distal end portion of the shaft when the sheath assembly is in the second position.

3. A system according to claim 1, wherein the first port comprises a plurality of ports that are located axially adjacent the distal end portion of the shaft and axially spaced from the electrode assembly.

4. A system according to claim 1, wherein the sheath assembly comprises a tube that is slidably movable relative to and concentric with the shaft, the tube defining an outer lumen between the tube and the shaft and the at least one radial seal being disposed between an outer surface of the shaft and an inner surface of the tube and sealingly engaging the shaft and the tube.

5. A system according to claim 4, wherein the at least one radial seal comprises a plurality of o-rings that are seated in an axial series of radial grooves formed in the inner surface of the tube, the radial grooves being axially spaced from each other.

6. A system according to claim 1, the first position operable to deliver fluid at a distance spaced away from the electrode assembly and the second position operable to deliver fluid adjacent to the active electrode.

7. A system according to claim 1, wherein the sheath assembly has a range of motion between the first and second positions that provides a variable level of fluid delivery, from a minimal level of fluid delivery in the first position, to a maximum level of fluid delivery in the second position.

8. A system for treating tissue, comprising:
an electrosurgical instrument having a shaft with a proximal end and a distal end portion;
an electrode assembly positioned on the distal end portion of the shaft comprising at least one active electrode and at least one return electrode axially spaced from the at least one active electrode;
a fluid delivery element for delivering electrically conductive fluid to the active electrode; and
a sheath assembly disposed adjacently to the fluid delivery element, the sheath assembly being axially moveable relative to the fluid delivery element from a first position to a second position;
wherein the fluid delivery element comprises an inner lumen extending through a portion of the shaft, and first and second ports extending radially through the shaft in fluid communication with the inner lumen, the first and second ports axially spaced apart; and
wherein the sheath assembly comprises a tube that is slidably movable relative to and concentric with the shaft, the tube defining an outer lumen between the tube and the shaft and having at least one radial seal, the at least one radial seal being disposed in the outer lumen between an outer surface of the shaft and an inner surface of the tube and sealingly engaging the shaft and the tube;
and further comprising a fluid source connected to the outer lumen proximal to the radial seal and, when the sheath assembly is in the second position, the fluid source provides a sequential fluid delivery path through the outer lumen proximal to the radial seal, the first port, the inner lumen, the second port, the outer lumen that is distal to the radial seal and via a distal opening disposed at the distal end of the shaft.

9. A system according to claim 1, wherein the first and second ports each comprise a plurality of ports, with the second port being located adjacent the distal end portion of the shaft and axially spaced from the electrode assembly, and the first port being located proximal to the second port.

10. A system according to claim 1, wherein the electrode assembly comprises an ablation electrode and a coagulation electrode, wherein the ablation electrode and the coagulation electrode are spaced axially from the return electrode.

11. An electrosurgical instrument for removing tissue from a target site within or on a patient's body comprising:
a shaft having proximal and distal end portion;
an electrode assembly comprising at least one active electrode positioned on the distal end portion of the shaft and a return electrode positioned on the shaft and axially spaced from the at least one active electrode;
a fluid delivery element for delivering fluid to the target site, the fluid delivery element comprising an inner lumen disposed along a portion of the shaft and a first and second plurality of orts extending radially through the shaft, the plurality of ports in fluid communication with the inner lumen;
a movable sheath assembly disposed adjacent to the shaft and defining an annular space around the shaft, the annular space having at least one radial seal disposed therein, the sheath assembly having a leading edge and being movable from a first position wherein the leading edge is retracted proximally from the electrode assembly to a second position wherein the leading edge is adjacent to the electrode assembly;
wherein the first and second plurality of ports are fluidly bypassed in the first position.

12. The electrosurgical instrument of claim 11, wherein the sheath assembly comprises a tube that is slidably movable relative to and concentric with the shaft, the tube defining an outer lumen between the tube and the shaft, the at least one radial seal being disposed between an outer surface of the shaft and an inner surface of the tube and sealingly engaging the shaft and the tube.

13. An electrosurgical instrument for removing tissue from a target site within or on a patient's body comprising:
a shaft having proximal and distal end portions;
an electrode assembly comprising at least one active electrode positioned on the distal end portion of the shaft and a return electrode positioned on the shaft and axially spaced from the at least one active electrode;
a movable sheath assembly disposed adjacent to the shaft and defining an annular space around the shaft, the sheath assembly having a leading edge and being movable from a first position wherein the leading edge is retracted proximally from the electrode assembly to a second position wherein the leading edge is adjacent to the electrode assembly, wherein the sheath assembly comprises a tube that is slidably movable relative to and concentric with the shaft, the tube defining an outer lumen between the tube and the shaft and having at least one radial seal, the at least one radial seal being disposed between an outer surface of the shaft and an inner surface of the tube and sealingly engaging the shaft and the tube;
a fluid delivery element for delivering fluid to the target site; said delivery element comprising an inner lumen disposed along a portion of the shaft and a plurality of ports extending radially through the shaft, the plurality of ports in fluid communication with the inner lumen and the annular space;
wherein the first and second plurality of ports are fluidly bypassed in the first position, and wherein the first and second plurality of ports are fluidly connected to the outer lumen proximal to at least one radial seal in the second position.

14. A system according to claim 11, wherein the electrode assembly comprises at least one ablation electrode and at least one coagulation electrode located on the shaft, wherein the ablation electrode and the coagulation electrode are axially spaced from the return electrode.

15. A system according to claim 11, wherein the sheath assembly further comprises a grip operable to slide the sheath assembly into position.

* * * * *